US00PP09805P

United States Patent [19]

van der Meer

[11] Patent Number: Plant 9,805

[45] Date of Patent: Feb. 18, 1997

[54] HYBRID TEA ROSE PLANT NAMED 'SELTANTALIUM'

[75] Inventor: Peter J. A. van der Meer, Withcorn, Netherlands

[73] Assignee: Terra Nigra Holding B.V., De Kwakel, Netherlands

[21] Appl. No.: 591,387

[22] Filed: Jan. 25, 1996

[51] Int. Cl.[6] ..... A01H 5/00

[52] U.S. Cl. ..... Plt./11

[58] Field of Search ..... Plt./11, 20, 21

[56] References Cited

U.S. PATENT DOCUMENTS

P.P. 8,055 12/1992 Boerlage ..... Plt./14

*Primary Examiner*—Howard J. Locker

[57] ABSTRACT

A new rose variety of the Hybrid Tea class, characterized by its continuous production of red/purple large flowers, borne singly on upright stems on a bush of medium height (120–150 cm) and that is especially suitable for growing in Latin America considering the prevailing light intensity, day length and seasonal effects.

2 Drawing Sheets

BACKGROUND OF THE INVENTION

The present invention relates to a new and distinct variety of rose plant of the Hybrid Tea class, which was originated by me by crossing the variety 'Tineke', which is subject of U.S. Plant Pat. No. 8,055, with an unnamed seedling (SR 4063).

The primary objective of this breeding was to obtain a new large type rose with a good presentation and bud shape in different colors. The main difference between its parent 'Tineke' is its red/purple color of the flower. The other parent (SR 4063) is not able to perform well in Latin America and has less rapid flowering cycles. Among the novel characteristics possessed by the new variety which distinguish it from all other varieties of which I am aware are:

(1) A vary large flower and flowerbud.

(2) The red/purple color of the flower.

(3) Rapid flowering cycles.

(4) Suitability for growing in Latin America.

(5) A vigorous upright plant of medium height (120–150 cm).

Asexual reproduction of the new rose variety by cutting and grafting using *R. canina* 'Inermis' as rootstock, as performed in a greenhouse in Quito, Ecuador, shows that the aforementioned characteristics and distinctions come true to form and are established and transmitted through succeeding propagations.

BRIEF DESCRIPTION OF THE DRAWINGS

The new variety of rose plant is illustrated by the accompanying photographic illustrations, of which:

Sheet 1 shows a full face view of the flower and

Sheet 2 shows a typical specimens of the vegetative growth and flowers of the new variety in different stages of development and as depicted in color as nearly true as it reasonably possible to make the same in color illustrations of this character.

The following is a detailed description of this new variety, with color terminology in accordance with The Royal Horticultural Society Colour Chart (R.H.S.C.C.). The terminology used in the color description herein refers to plate numbers in the aforementioned color chart e.g. "55C" is plate "55C" of The Royal Horticultural Society Colour Chart.

Parentage: Seedling.

*Seed parent.*—'Tineke'.

*Pollen parent.*—Unnamed seedling SR 4063.

Classification:

*Commercial.*—Hybrid Tea.

BOTANICAL DESCRIPTION OF THE PLANT

Flower (Observations made from specimens grown in a greenhouse in Quito, Ecuador)

Blooming habit of Seltantalium: Almost continuous.

Time of beginning of flowering: Early.

A. Bud:

(1) *Size.*—Large. Diameter 3.5–4.0 cm. Length 6.5–7.0 cm.

(2) *Form.*—Egg shaped (Long); is not affected by wet or hot weather.

(3) *Color.*—When the sepals first divide, the color of the outside is red/purple 63A.

(4) *Sepals.*—Length: 45 to 50 mm. Slightly branched, curl back when petals start to unfurl. Color: inside: 144A flushed with 63A. outside: 143A.

(5) *Calyx.*—Color: 143C. Shape: pear. Size: large. Aspect: glandular. Odor when rubbed: no.

(6) *Rate of opening.*—Normal to rapid.

(7) *Peduncle.*—Length: medium, 5 to 6 cm. Aspect: glandular with very few and very small prickles. Strength: strong. Color: 143C overlaid with 59B.

(8) *Opening.*—Opens up well; is not affected by adverse weather.

B. Bloom:

(1) *Size.*—Large; when fully expanded about 13 cm in diameter with a depth of about 7 cm.

(2) *Borne.*—Single.

(3) *Stems.*—Length: long. Strength: strong.

(4) *Form (when first open).*—Irregular ovoid. Permanence: will flatten when aging.

(5) *Petalage.*—Number of petals: average 40.

(6) *Color.*—Center of flower: 63B. Outer petals: 67B. Base of petals: 4D with a small yellow spot at the base 2B on the innerside mostly. Inside of petals: 67B. Reverse of petals: at base: 8C, higher zones 67B. General tonality: 67B.

(7) *Discoloration.*—General tonality 67B fading to 67D.

C. Petals:

(1) *Texture.*—Leathery; is not affected by wet or hot weather.

(2) *Appearance.*—Inside: velvety. Outside: satiny.

(3) *Form.*—Broad obovate.

(4) *Arrangement.*—Irregular.

(5) *Petaloids in center.*—Number: average 2. Size: large. Color: 46A.

(6) *Persistance.*—Drop off cleanly.

(7) *Fragrance.*—Little; Honey-like scent.

(8) *Lasting quality.*—As cutflower: 10 days. On the plant: good.

Reproductive Organs

A. Stamens:

(1) *Arrangement.*—Regularly around styles.

(2) *Number.*—Average close to 230.

(3) *Length.*—11 to 14 mm.

(4) *Anthers.*—Size: medium, 3 to 4 mm. Color: 20A.

(5) *Filaments.*—Length: medium, 8 to 10 mm. Color: base of anthers 48B, lower filament 4D.

(6) *Pollen.*—Color: yellow.

B. Pistils:

(1) *Styles.*—Number: average close to 200. Length: large 9 to 12 mm. Color: Base: 4D. Top spotted with 48B.

(2) *Stigmas.*—Color: 18A.

(3) *Fruit.*—Fertility: Unknown. Hips: not observed.

Plant

A. Form: Greenhouse rose.

B. Growth: Vigorous upright.

Height: Medium, 120 to 150 cm.

Foliage: Compound of 1, 3, 5 or 7 leaflets. Average 8 to 10 compound leaves on bloom stem, 10 to 12 on main canes.

(1) *Size.*—12 to 20 cm.

(2) *Quantity.*—Stem covering, abundant.

(3) *Color.*—New foliage: upper side: 137B. under side: 138B. Old foliage: upper side: 137A. under side: 138A+B.

(3) *Texture.*—Upper side: leathery, dull. Underside: leathery, dull.

(4) *Terminal leaflet.*—Shape: oval pointed, base obtuse. Size: large. Length 10.5 to 11 cm. Diameter 6 to 6.5 cm. Length petiole 1.5 to 2 cm.

(5) *Ribs and veins.*—Veins with anthocyanin coloration.

(6) *Ranchis.*—Upper side: very few glandular hairs. Lower side: 2 to 4 mm sized hooked prickles, 2 to 4 per compound leaf.

(7) *Margin type.*—Strongly serrate, 2 points/cm, 2 to 3 mm peak.

(8) *Stipules.*—Length: average 20 to 30 mm, auricle to 5 mm. Texture: smooth, glandular hairs at outer edge. Color: 143C.

E. Resistance to diseases: Average.

F. Wood:

(1) *New wood.*—Color: purple brownish; 200D. Bark: smooth.

(2) *Old wood.*—Color: green and a little bronze. Bark: smooth.

G. Thorns:

(1) *Quantity.*—Medium.

(2) *Form.*—Upperside concave. Lower side deep concave.

(3) *Length.*—Average 6 to 8 mm.

(4) *Hooked.*—Downward.

(5) *Color (when young).*—Red purple; 182A.

(6) *Position.*—Irregular, starting from 20 to 25 cm below bloom.

H. Prickles:

*Quantity.*—On peduncle: none. On rachis: 2 to 4 per compound leaf.

I. Short needles:

*Quantity.*—Very few on peduncle and rachis.

I claim:

1. A new and distinct variety of rose plant of the Hybrid Tea class, substantially as herein shown and described characterized particularly as to novelty by its large red/purple flowers, borne singly on strong, upright stems especially suitable for growing in Latin America.

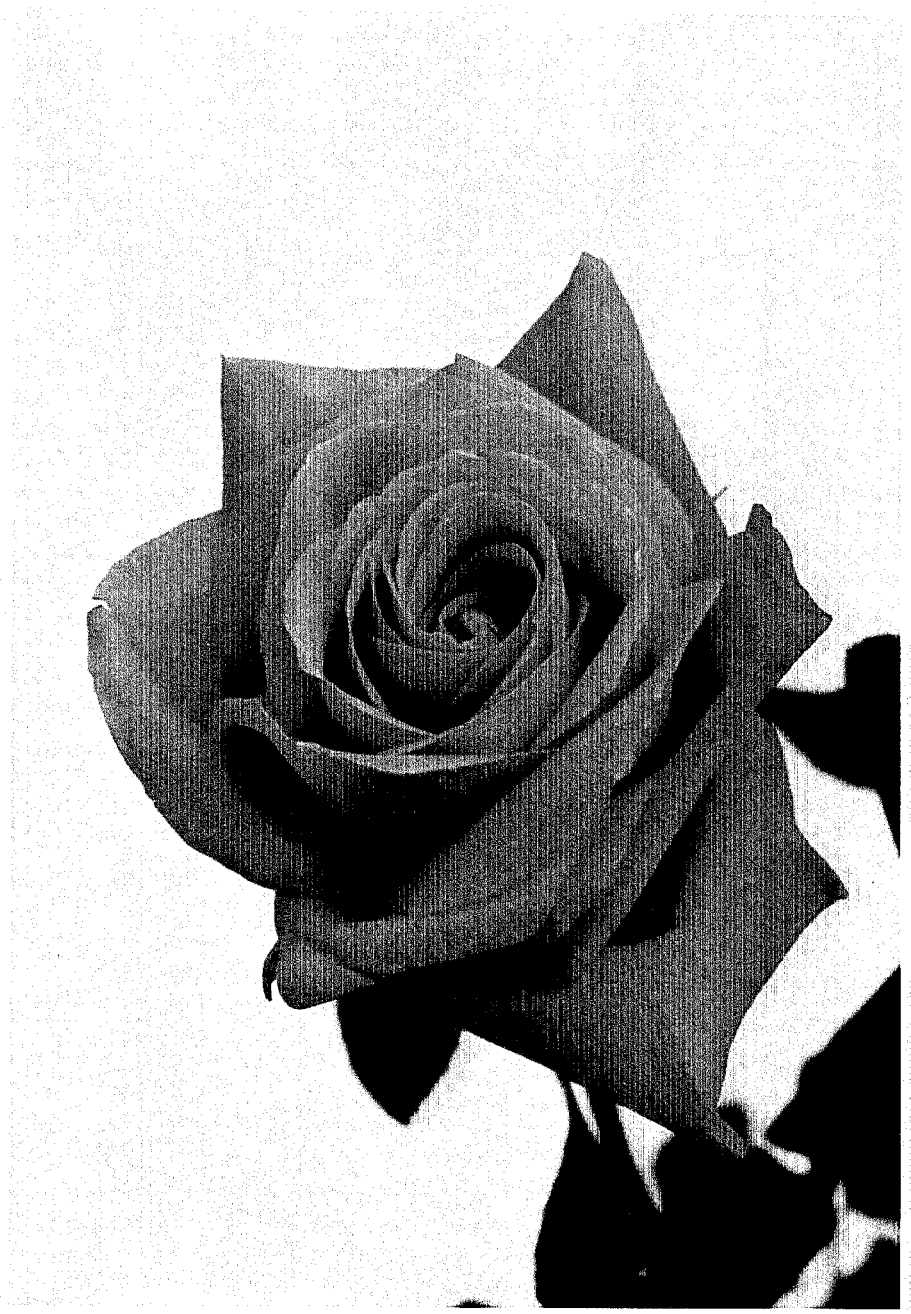

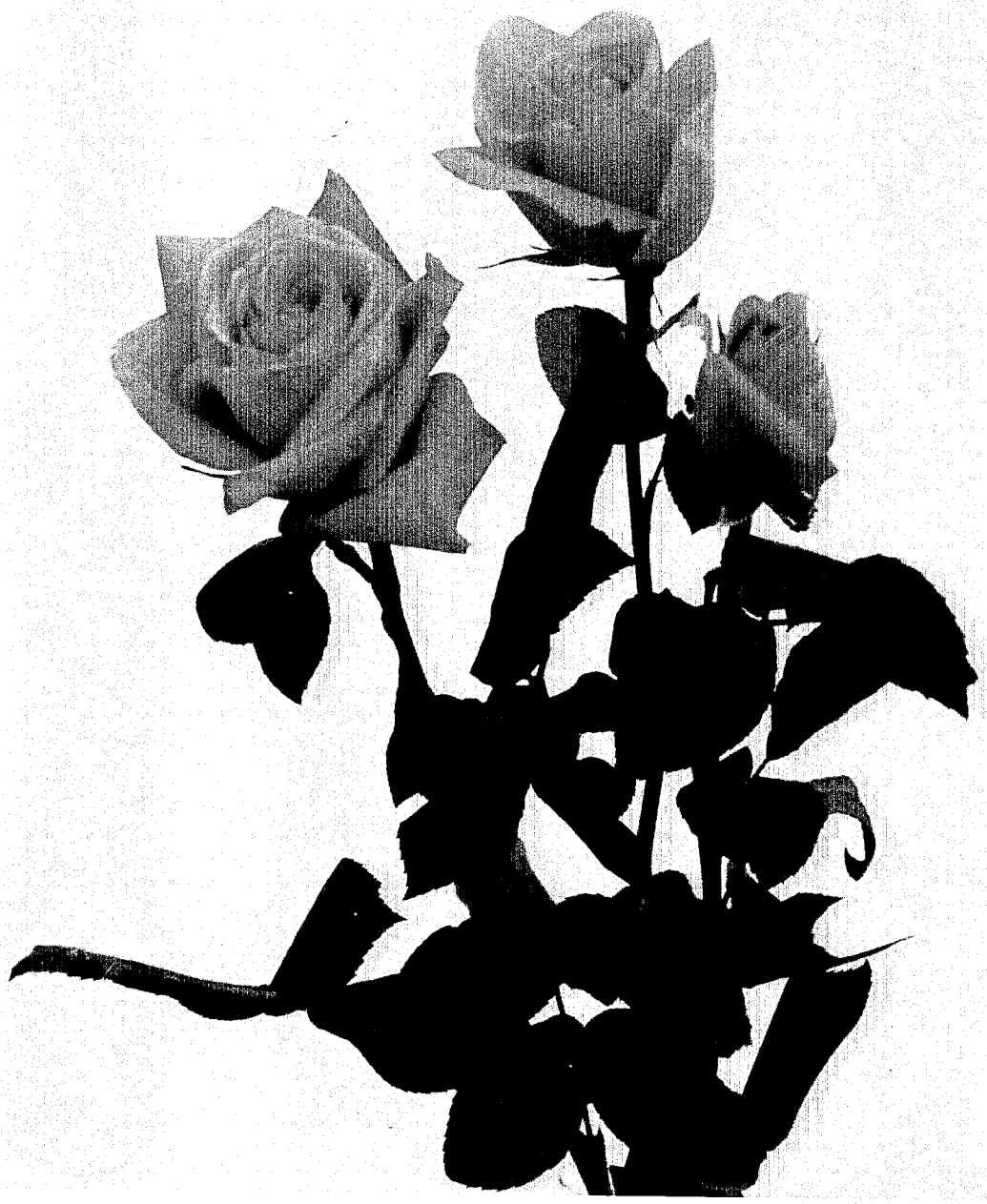

* * * * *